United States Patent [19] [11] Patent Number: 5,011,854
Takahashi et al. [45] Date of Patent: Apr. 30, 1991

[54] HYDROXAMIC ACID DERIVATIVES AND USE THEREOF IN COMBATTING LIPOXYGENASE-MEDIATED DISEASES

[75] Inventors: Mitsuru Takahashi, Kanagawa; Shigeto Kitamura; Hiroshi Kase, both of Tokyo; Masaji Kasai; Isao Kawamoto, both of Kanagawa; Takao Iida; Hiroshi Sano, both of Tokyo; Hiromitsu Saito, Kanagawa; Koji Yamada, Tokyo; Chikara Murakata, Saitama, all of Japan

[73] Assignee: Kyowa Hakko Kogyo Co. Ltd., Tokyo, Japan

[21] Appl. No.: 281,050

[22] Filed: Dec. 7, 1989

[30] Foreign Application Priority Data

Sep. 12, 1987 [JP] Japan .............................. 62-311692

[51] Int. Cl.⁵ .................... A61K 31/24; A61K 31/16; C07C 233/00; C07C 235/00
[52] U.S. Cl. .................................... 514/541; 564/224; 564/219; 564/215; 514/629; 514/575; 514/630; 514/555; 562/622; 562/623; 560/168; 560/35

[58] Field of Search ......... 564/224, 219, 215; 514/629, 575, 630, 541, 555; 260/500.5 H; 562/622, 623; 560/168, 35

[56] References Cited

U.S. PATENT DOCUMENTS 4,270,001 5/1981 Redmore et al. .................... 564/224

Primary Examiner—Mary C. Lee
Assistant Examiner—Robert C. Whittenbaugh
Attorney, Agent, or Firm—Nixon & Vanderhye

[57] ABSTRACT

A hydroxamic acid compound represented by the general formula (I) or a salt thereof;

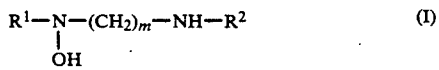

$$R^1-\underset{OH}{N}-(CH_2)_m-NH-R^2 \qquad (I)$$

wherein $R^1$ represents a hydrogen atom, or a substituted or unsubstituted alkanoyl group, $R^2$ represents an unsubstituted alkanoyl, substituted lower alkanoyl or substituted lower alkyl group, and m represents an integer of 3 to 7, which are useful for the prevention and/or treatment of diseases caused by lipoxygenase-mediated metablites.

7 Claims, No Drawings

HYDROXAMIC ACID DERIVATIVES AND USE THEREOF IN COMBATTING LIPOXYGENASE-MEDIATED DISEASES

FIELD OF THE INVENTION

This invention relates to novel hydroxamic acid derivatives. The compounds provided by the present invention can be used in the prevention and/or treatment of diseases caused by lipoxygenase-mediated metabolites.

BACKGROUND OF THE INVENTION

Lipoxygenases (E.C. 1.13.11.12) are enzymes occurring in platelets, leukocytes, lymphocytes, etc., and converting polyunsaturated fatty acids (in particular arachidonic acid) to hydroperoxides. The positions 5, 8, 9, 11, 12 and 15 are known to be available for the introduction of a hydroperoxy group into arachidonic acid by lipoxygenases. Thus, for instance, the lipoxygenase occurring in relatively large amounts in platelets is 12-lipoxygenase which hydroperoxidizes arachidonic acid at the position 12, while 5-lipoxygenase and 15-lipoxygenase are reportedly present in leukocytes. Hydroperoxyeicosatetraenoic acids produced from arachidonic acid by the action of lipoxygenases are unstable and are converted to the corresponding hydroxyeicosatetraenoic acids.

Recent studies have revealed that these fatty acids which lipoxygenases produce and in vivo metabolites thereof have various physiological activities. For example, it has been demonstrated that the slow reacting substance of anaphylaxis which is produced in the lung of anaphylactic guinea pigs and in the human lung on the occasion of asthmatic attack and which causes contraction of the bronchial smooth muscle essentially consists of leukotrienes C, D, E and F which are 5-lipoxygenase-mediated metabolites of arachidonic acid [Samuelson et al., Proc. Natl. Acad. Sci., U.S.A., 77, 2014 (1980)]. Further, 12-hydroperoxyeicosatetraenoic acid (12-HPETE) and 12-hydroxyeicosatetraenoic acid (12-HETE), which are 12-lipoxygenase-mediated metabolites, exhibit a variety of physiological activities, such as leukocyte migrating activity, neutrophil attracting activity, platelet thromboxane synthetase inhibiting activity, prostacycline synthetase inhibiting activity and smooth muscle cell migrating activity [cf. Seiitsu Murota (ed.), Prostaglandin to Byotai (Prostaglandins and Pathology), published by Tokyo Kagaku Dojin, 1984].

As mentioned above, it has been reported that the lipoxygenase-mediated metabolites cause stimulation of peripheral blood vessel permeability, leukocytotaxis, and contraction of various types of smooth muscle such as the smooth muscle of the respiratory system (trachea, bronchi, lung tissues), vascular system or digestive system. Thus, the lipoxygenase-mediated metabolites have been considered to cause bronchial asthma, allergic diseases (atopic dermatitis, inflammation of organs, etc.) and diseases of the cirulatory system (edema, ischemic heart diseases, hypertension, ischemic encephalopathy, arteriosclerosis, etc.); they are also chemical mediators inducing inflammatory diseases. Therefore, artificial suppression of the lipoxygenase activity by means of some specific inhibitors might possibly lead to successful prevention and/or treatment of the above-mentioned diseases.

Among compounds known to have lipoxygenase inhibiting activity, there are AA-861, BW-755C, etc. Pharmacologically, BW-755C has anti-inflammatory and other activities and AA-861 has bronchial contraction suppressing, anti-inflammatory, anti-myocardiac infarction and other activities [T. Yoshimoto et al., Biochim. Biophys. Acta, 713, 470 (1982); G.A. Higgs et al., Biochem. Pharmacol., 28, 1959 (1975); Y. Maki et al., Prostaglandins, 26 (6), 955 (1983); K. Sasaki et al., Adv. Prostaglandin, Thromboxane & Leukotriene Res., 17, 381 (1987)].

U.S. Pat. Nos. 4,623,661, 4,604,407, 4,608,390, 4,605,669, 4,738,986, 4,771,038, 4,728,670 EP-A-254 852 and GB-A-2 189 486 disclose certain hydroxamic acid derivatives having lipoxygenase inhibiting activity.

H. Bickel et al., Helv. Chim. Acta., 43, 2129 (1960) and S. Adapa et al., ibid., 65, 1818 (1982) describe desferri-ferrioxamines having the following formulae:

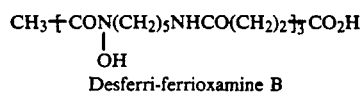

Desferri-ferrioxamine B

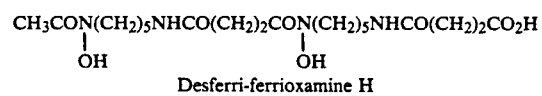

Desferri-ferrioxamine H

The desferri-ferrioxamines are compounds derivable from the corresponding ferrioxamines isolated from actinomycete fermentation products as growth factors for microorganisms, by removal of the iron atom therefrom. The reports so far published on the ferrioxamines and desferri-ferrioxamines do not make any mention of the lipoxygenase inhibiting activity.

Hithertofore, several types of lipoxygenase inhibiting compounds have been reported. In most cases, however, the inhibitory activity is relatively low or is non-specific, namely poorly distinguishable from the inhibitory activity against other enzymes [cf. T. Schewe et al., Adv. Enzymol., 58, 191 (1986)]. Accordingly, the development of better lipoxygenase inhibitors which have high inhibitory activity and can remain effective in vivo has been awaited.

SUMMARY OF THE INVENTION

An object of the present invention is to provide novel hydroxamic acid derivatives having potent lipoxygenase inhibiting activity which are useful for the prevention and/or treatment of diseases caused by lipoxygenase-mediated metabolites.

As a result of intensive investigation to achieve the above objects, it has now been found that the above and other objects can be accomplished by a novel hydroxamic acid compound, inclusive of salts thereof, of the general formula (I)

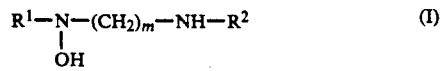

wherein $R^1$ represents a hydrogen atom, or a substituted or unsubstituted alkanoyl group, $R^2$ represents an unsubstituted alkanoyl, substituted lower alkanoyl or substituted lower alkyl group, and m represents an integer of 3 to 7. The compounds represented by formula (I) are hereinafter referred to as "Compounds (I)".

DETAILED DESCRIPTION OF THE INVENTION

Referring to formula (I), the alkyl moiety of the alkanoyl group includes a straight or branched alkyl group having 1 to 17 carbon atoms. Specific examples thereof include methyl, ethyl, n-propyl, isopropyl, n-butyl, isobutyl, n-pentyl, n-hexyl, n-heptyl, n-octyl, n-nonyl, n-decyl, n-undecyl, 9-methyldecyl, n-dodecyl, 9-methylundecyl, 10-methylundecyl, n-tridecyl, 11-methyldodecyl, n-tetradecyl, 11-methyltridecyl, 12-methyltridecyl, n-pentadecyl, 13-methyltetradecyl, n-hexadecyl, n-heptadecyl, etc.

The alkyl moiety of the lower alkanoyl group and the lower alkyl group include an alkyl group having 1 to 5 carbon atoms, for example, methyl, ethyl, n-propyl, isopropyl, n-butyl, isobutyl, n-pentyl, etc.

The substituent on the substituted alkanoyl, substituted lower alkanoyl and substituted lower alkyl groups is a hydroxycarbonyl group or a lower alkoxycarbonyl group.

The lower alkoxy moiety of the lower alkoxycarbonyl group is an alkoxy group having 1 to 5 carbon atoms, for example, methoxy, ethoxy, n-propoxy, isopropoxy, n-butoxy, isobutoxy, n-pentyloxy, etc.

When Compounds (I) are acidic compounds, they can form base addition salts, inclusive of salts with metals, whereas when they are basic compounds, they can form acid addition salts. Specific examples of the base addition salts include ammonium salt, salts of an alkali metal (e.g., lithium, sodium, or potassium), salts of an alkaline earth metal (e.g., calcium or magnesium), salts of an organic amine (e.g., triethylamine, morpholine, piperidine or dicyclohexylamine) and salts of a basic amino acid (e.g., arginine or lysine). Specific examples of the acid addition salts of Compounds (I) are salts of hydrochloric acid, hydrobromic acid, sulfuric acid, nitric acid, formic acid, acetic acid, benzoic acid, maleic acid, fumaric acid, succinic acid, tartaric acid, citric acid, oxalic acid, methanesulfonic acid, toluenesulfonic acid, aspartic acid or glutamic acid. While pharmacologically acceptable nontoxic salts are preferred, other salts are also useful in the step of product isolation and/or purification.

Compound (I) can be produced by the processes described below.

In the following description, the notations (I-1), (I-2) and so on mean that the compounds indicated thereby are included in the category of Compounds (I) and the notations (I-2)a, (I-7)a, (I-8)a and so on mean that the compounds indicated thereby are included in Compounds (I-2), (I-7), (I-8) and so on, respectively.

Further, in the following reaction formulae, the notations Et, i-Pr and φ represent an ethyl group, an isopropyl group and a phenyl group, respectively.

Six processes (A to F) may be mentioned for the synthesis of Compounds (I) classified according to substituents. The relationships between the processes and the number of compounds are as follows:

| Process | Compound No. | Substituent |
|---|---|---|
| A | I-1 | $R^1$ = H |
| B | (I-2)a | $R^1$ = [α]-substituted alkanoyl |
|   | I-3 | $R^1$ = [β]-substituted alkanoyl |
| C | I-4 | $R^1$ = alkanoyl |
| D | I-5 | $R^2$ = [β]-substituted alkyl |
|   | I-6 | $R^2$ = [α]-substituted alkyl |
| E | I-7 | $R^2$ = [α]-substituted alkanoyl |
| F | I-8 | $R^2$ = [β]-substituted alkanoyl |
|   | I-9 | $R^1$ = H or alkanoyl and $R^2$ = substituted alkanoyl |

[α] = lower alkoxycarbonyl
[β] = hydroxycarbonyl

Process A

Compounds (I-1) wherein $R^1$ in formula (I) is a hydrogen atom can be synthesized by the following [Steps 1-1 to 1-4].

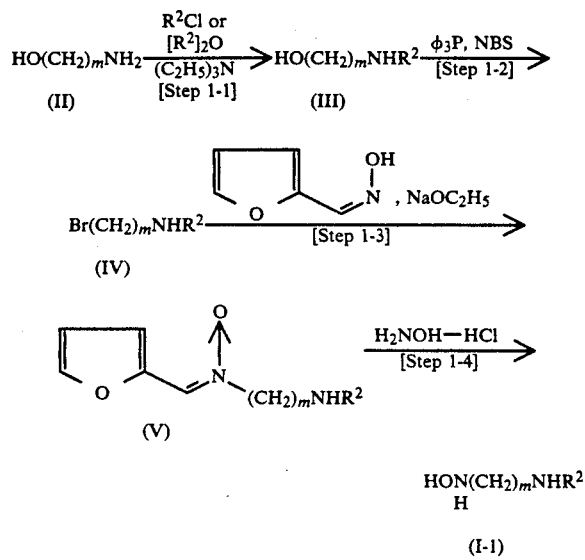

In the above formulae, m and $R^2$ are as defined

Step 1-1

Compound (II) (aminoalcohol) is allowed to react with an acid chloride or acid anhydride in a solvent inert to the reaction, for example, tetrahydrofuran (THF), in the presence of a base, for example, triethylamine, at 0° C. to room temperature for 1 to 3 hours to give Compound (III) (amidoalcohol). The acid chloride or acid anhydride is used in an amount of 1 equivalent and the base in an amount of 1 to 1.5 equivalents relative to Compound (II).

Step 1-2

Compound (III) is then allowed to react with N-bromosuccinimide (NBS) in the presence of triphenylphosphine in a solvent inert to the reaction, for example, dichloromethane, overnight at 0° C. to room temperature to give Compound (IV). Triphenylphosphine and NBS are used each in an amount of 2 equivalents relative to Compound (III).

Step 1-3

Compound (IV) is allowed to react with (Z)-2-furaldehyde oxime in a solvent inert to the reaction, for example, ethanol, in the presence of a base, for ample, sodium ethylate, at 40° C. to 50° C. for 2 to 5 hours to give Compound (V). (Z)-2-Furaldehyde oxime and sodium ethylate are used each in an amount of 1 equivalent relative to Compound (IV).

Step 1-4

Compound (V) is then allowed to react with hydroxylamine hydrochloride in a solvent inert to the reaction, for example, a mixture of water and methanol, at room temperature to 60° C. for 1 to 2 days to give Compound (I-1). Hydroxylamine hydrochloride is used in an amount of 1 to 2 equivalents relative to Compound (V).

Process B

Compounds (I-2)a wherein $R^1$ in formula (I) is a lower alkoxycarbonyl-substituted lower alkanoyl group can be synthesized in the [Step 2] shown below, and Compounds (I-3) in which $R_1$ in formula (I) is a hydroxycarbonyl-substituted lower alkanoyl group can be synthesized in the [Step 3] illustrated below. Compounds (I-2)b having an alkyl group $R^{3b}$ which is different from the alkyl group $R^{3a}$ in Compound (I-2)a can be synthesized in the following [Step 4].

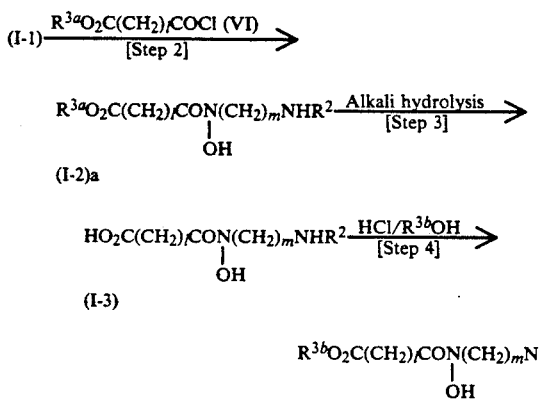

In the above formulae, m and $R^2$ are as defined above, l is an integer of 1 to 4, and $R^{3a}$ and $R^{3b}$, which are different, each represents a straight or branched alkyl group having 1 to 5 carbon atoms.

Step 2

Compound (I-1) is allowed to react with an acid chloride (VI) in a solvent inert to the reaction, for example, THF, at 0° C. to room temperature for 2 to 5 hours to give Compound (I-2)a. The acid chloride is used in an amount of 1 to 3 equivalents relative to Compound (I-1).

Step 3

Alkali hydrolysis of Compound (I-2)a in a solvent inert to the reaction, for example, methanol, gives Compound (I-3). Generally, sodium hydroxide, potassium hydroxide or the like is used as the source of alkali in large excess (5 equivalents or more) relative to Compound (I-2). The reaction is generally carried out at 0° C. to room temperature and is complete for 2 to 5 hours. Treatment of the resulting alkali metal salt with an acid gives Compound (I-3) which is the desired carboxylic acid.

Step 4

Compound (I-3) is allowed to react in an alcohol $R^{3b}OH$ in the presence of an appropriate acid, for example, hydrochloric acid, at 0° C. to room temperature for 2 hours to give Compound (I-2)b. The alcohol $R^{3b}OH$ is used in large excess (10 equivalents or more) relative to Compound (I-3).

Process C

Compounds (I-4) wherein $R^1$ in formula (I) is an alkanoyl group can be synthesized by the following [Step 5].

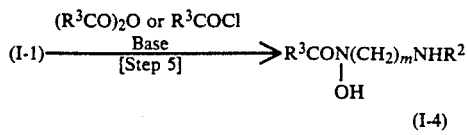

In the above formulae, m and $R^2$ are as defined above, $R^3$ is a straight of branched alkyl group having 1 to 17 carbon atoms.

Step 5

Compound (I-1) is allowed to react with an acid anhydride or acid chloride in a solvent inert to the reaction, for example, THF, in the presence of an appropriate base, for example, pyridine, at 0° C. to room temperature for 2 to 5 hours to give Compound (I-4). The acid anhydride or acid chloride is used in an amount of 1 to 3 equivalents and the base is used in an amount of 1 to 3 equivalents relative to Compound (I-1).

Process D

Compound (I-5) wherein $R^2$ in formula (I) is a hydroxycarbonyl-substituted lower alkyl group and Compounds (I-6) in which $R^2$ is a lower alkoxycarbonyl-substituted lower alkyl group can be synthesized by the following steps, [Step 6] and [Step 7], respectively.

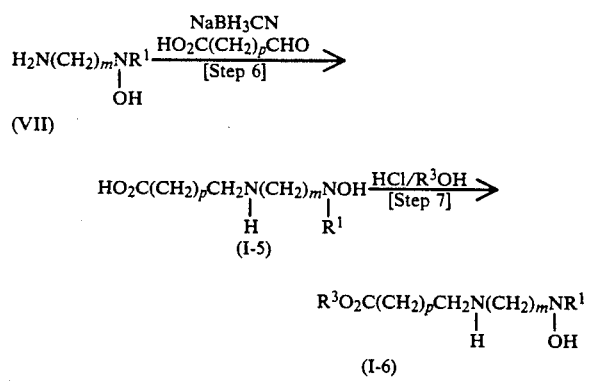

In the above formulae, m, $R^1$ and $R^3$ are as defined above and p is an integer of 1 to 4.

Step 6

Compound (VII) is allowed to react with an aldehyde (VIII) in a solvent inert to the reaction, for example, ethanol, in the presence of an appropriate reducing agent, for example, sodium cyanoborohydride, overnight at 0° C. to room temperature to give Compound (I-5). The aldehyde (VIII) is used in an amount of 1 to 3 equivalents and the reducing agent in an amount of 2 to 5 equivalents relative to Compound (VII).

Step 7

The procedure as in [Step 4] is repeated except for using Compound (I-5) in place of Compound (I-3) to give Compound (I-6).

Process E

Compounds (I-7) wherein $R^2$ in formula (I) is a lower alkoxycarbonyl-substituted lower alkanoyl group can be synthesized in the [Step 8] shown below, and Compound (I-8) wherein $R^2$ in formula (I) is a hydroxycarbonyl-substituted lower alkanoyl group can be synthesized in the [Step 9] shown below.

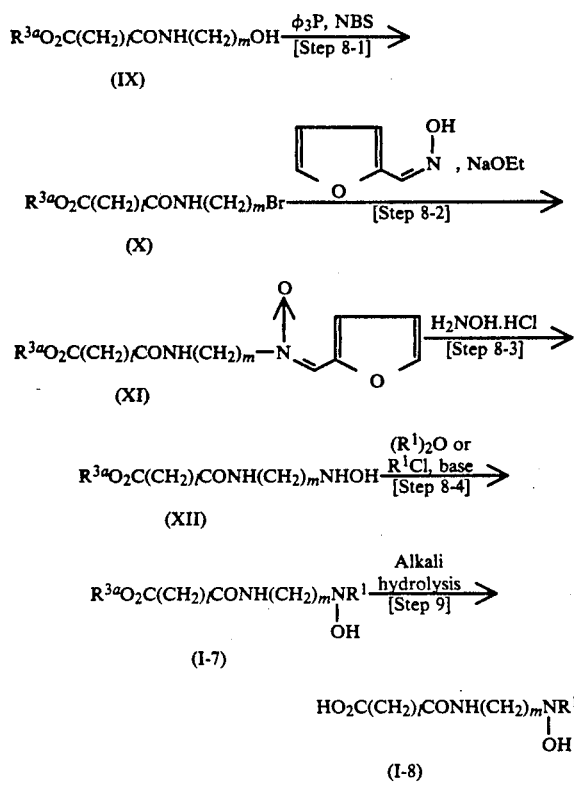

(IX)

(X)

(XI)

(XII)

(I-7)

(I-8)

In the above formulae, m, l, $R^1$ and $R^{3a}$ are as defined above.

Step 8

The same procedures as in [Step 1-2] to [Step 1-4] are repeated except for using Compound (IX) in place of Compound (III) to give Compound (XII) [Step 8-1 to Step 8-3].

The same procedure as in [Step 5] is repeated except for using Compound (XII) in place of Compound (I-1) and using $(R^1)_2O$ or $R^1Cl$ in place of $(R^3CO)_2O$ or $R^3COCl$, respectively, to give Compound (I-7) [Step 8-4].

Step 9

The same procedure as in [Step 3] is repeated except for using Compound (I-7) in place of Compound (I-2)a to give Compound (I-8).

Compound (I-9) having an alkyl group $R^{3b}$ which is different from $R^{3a}$ in Compound (I-7) can be synthesized by the following [Step 10].

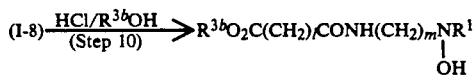

In the above formulae, $R^1$, $R^{3b}$, l and m are as defined above.

Step 10

The same procedure as in [Step 4] is repeated except for using Compound (I-8) in place of Compound (I-3) to give Compound (I-9).

In addition to [Steps 8 and 9], the following steps are available for the synthesis of compounds (I-8)a and (I-7)a in which $R^2$ is a hydroxycarbonyl-substituted lower alkanoyl group [Step 11-1 and Step 11-2] or a lower alkoxycarbonyl-substituted lower alkanoyl group [Step 12].

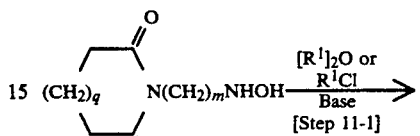

(XIII)

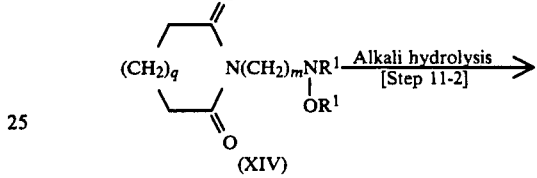

(XIV)

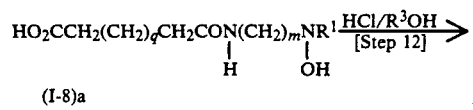

(I-8)a $R^3O_2CCH_2(CH_2)_qCH_2CONH(CH_2)_mNR^1$
                                    |
                                    OH (I-7)a

In the above formulae, l, m, $R^1$ and $R^3$ are as defined above and q is an integer of 0 to 3.

Step 11

The same procedure as in [Step 5] is repeated except for using Compound (XIII) in place of Compound (I-1) and using $(R^1)_2O$ and $R^1Cl$ in place of $(R^3CO)_2O$ and $R^3COCl$, respectively, to give Compound (XIV) [Step 11-1].

The same procedure as in [Step 3] is repeated except for using Compound (XIV) in place of Compound (I-2)a to give Compound (I-8)a [Step 11-2].

Step 12

The same procedure as in [Step 4] is repeated except for using Compound (I-8)a in place of Compound (I-3) to give Compound (I-7)a.

Process F

Compounds (I-9) wherein in formula (I), $R^1$ is a hydrogen atom or an alkanoyl group and $R^2$ is a substituted alkanoyl group can be synthesized by the following [Steps 13 to 18].

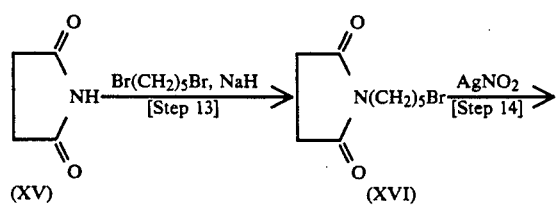

(XV)                              (XVI)

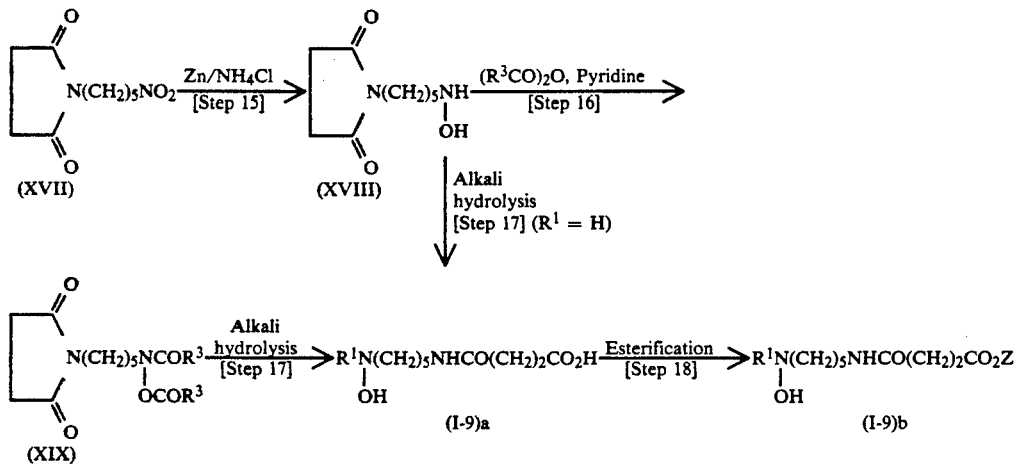

In the above formulae, $R^1$, $R^2$ and $R^3$ are as defined above and Z is a lower alkyl group.

Step 13

Reaction of succinimide with 1,5-dibromopentane in an inert solvent in the presence of sodium hydride is carried out to give Compound (XVI). 1,5-Dibromopentane and sodium hydride are generally used each in an amount of 1 to 2 equivalents relative to succinimide. Tetrahydrofuran (THF), N,N-dimethylformamide (DMF), etc., dehydrated by distillation, is used as the inert solvent. The reaction is generally carried out at a temperature of room temperature to 70° C. for 2 to 24 hours.

In this step as well as in the subsequent steps, produce isolation and purification may be performed by any of the techniques generally used in organic syntheses, for example, a combination of extraction, crystallization, chromatography and so on. The reaction mixture as such may be used as the raw material for the next step without purification.

Step 14

Compound (XVI) is allowed to react with silver nitrite (1 to 2 equivalents) in an inert solvent to give Compound (XVII). As the inert solvent, acetonitrile, nitromethane, nitropropane and nitrobenzene, etc. are used. The reaction is generally carried out at a temperature of room temperature to 150° C. for 2 to 24 hours.

Step 15

Reduction of Compound (XVII) with zinc/ammonium chloride is carried out to give Compound (XVIII). Zinc is used in an amount of 2 to 6 equivalents and ammonium chloride in an amount of 20 to 50 equivalents relative to Compound (XVII). The reaction is generally carried out at a temperature of 0° C. to room temperature for 10 minutes to 2 hours.

Step 16

For the production of the desired compounds in which $R^1=R^3CO$, Compound (XVIII) is allowed to react with an acid anhydride $(R^3CO)_2O$ in pyridine to give a diacylated Compound (XIX). When the acid anhydride has a low solubility in pyridine, a solvent such as methylene chloride or chloroform should preferably be added to the reaction system. The acid anhydride is generally used in an amount of 2 to 5 equivalents relative to Compound (XVIII). The reaction is carried out at a temperature of 0° C. to room temperature for 2 to 15 hours.

Step 17

For the production of the desired compounds in which $R^1=$H, Compound (XVIII) or Compound (XIX) obtained in [Step 16] is subjected to alkali hydrolysis to give alkali metal salt of Compound (I-9)a. Generally, sodium hydroxide, potassium hydroxide or the like is used as the alkali source in large excess (10 equivalents or more) relative to Compound (XVIII) or (XIX). For improved dissolution of Compound (XVIII) or (XIX), addition of methanol, THF, DMF or the like to the aqueous alkali is preferred. The reaction is generally carried out at a temperature of 0° C. to 50° C. for 2 hours or less. Acid treatment of the alkali metal salt thus formed gives the desired carboxylic acid (I-9)a.

Step 18

Esterification of the carboxylic acid (I-9)a is carried out to give compound (I-9)b. Use of a diazoalkane provides a simple and easy method of esterification. The diazoalkane is generally used in large excess (10 equivalents or more) relative to Compound (I-9)a. The reaction is generally carried out in an alcohol such as methanol or ethanol at a temperature of 0° C. to room temperature for 10 minutes to 2 hours.

On the other hand, those compounds of formula (I) in which $R^1$ is an alkanoyl group having 12 to 18 carbon atoms and $R^2$ is a methoxycarbonylpropanoyl group can also be obtained by cultivating in a nutrient medium an actinomycetous strain belonging to the genus Micromonospora and capable of producing said compounds, followed by recovery of said compounds from the culture (cf. Example 34). A typical example of such strain is Micromonospora sp. K-216.

The above described strain has been deposited at the Fermentation Research institute, Agency of Industrial Science and Technology, Ministry of International Trade and Industry, Japan of 1-3, Higashi 1-chome, Yatabe-machi, Tsukuba-gun, Ibaraki-ken, 305 Japan (hereinafter referred to as "Bikoken") by the International Depositary pursuant Budapest Treaty since Sept. 21, 1987 under the accession number FERM BP-1406.

The product isolation and purification after completion of each step mentioned above may be performed by those methods which are common in organic syntheses, for example, by a combination of extraction, crystallization, chromatography and so forth. The product may also be directly used as the starting material for the next step without purification.

Typical examples of the compounds according to the present invention are shown below in Table 1, together with some physical properties thereof.

TABLE 1

$$R^1-N-(CH_2)_m-NH-R^2$$
$$|$$
$$OH$$

| No. | $R^1$ | m | $R^2$ | Melting point (°C.) | A | $^1$H-NMR δ: ppm |
|---|---|---|---|---|---|---|
| 1 | H | 5 | $CO(CH_2)_{10}CH_3$ | | 301 $(M+1)^+$ | 0.76~1.00 (3H, m), 1.00~1.80 (24H, m), 2.18 (2H, t, J=8Hz), 2.90 (2H, t, J=7Hz), 3.00~3.32 (2H, m) |
| 2 | $CO(CH_2)_2COOCH_3$ | 5 | " | 93~94 | 415 $(M+1)^+$ | 0.76~1.00 (3H, m), 1.00~2.28 (26H, m), 2.48~2.92 (4H, m), 3.26 (2H, m), 3.64 (2H, t, J=7Hz), 3.67 (3H, s), 5.90 (1H, br s), 8.72 (1H, br. s) |
| 3 | $CO(CH_2)_2COOH$ | 5 | " | | 401 $(M+1)^+$ | 0.76~0.96 (3H, m), 1.00~1.92 (24H, m), 2.16 (2H, t, J=8Hz), 2.48~2.92 (4H, m), 3.08~3.32 (2H, m), 3.64 (2H, t, J=7Hz) |
| 4 | $CO(CH_2)_2CO_2i$-Pr | 5 | " | | 442 $(M^+)$ | 0.72~2.04 (24H, m), 2.19 (2H, t, J=8Hz), 2.50~2.92 (4H, m), 3.12~3.40 (2H, m), 3.66 (2H, t, J=7Hz), 5.00 (1H, m), 5.80 (1H, br. s) |
| 5 | $COCH_3$ | 5 | $CO(CH_2)_{10}CH_3$ | | 343 $(M+1)^+$ | 0.87 (3H, br. t, J=7Hz), 1.07~2.37 (26H, m), 3.03~3.47 (2H, m), 3.49~3.80 (2H, m), 5.87 (1H, br. s), 8.97 (1H, br. s) |
| 6 | $CO(CH_2)_{10}CH_3$ | 5 | $(CH_2)_3COOH$ | | 387 $(M+1)^+$ | 0.88 (3H, br. t, J=6Hz), 1.00~2.16 (20H, m), 2.32~2.64 (4H, m), 2.84~3.12 (4H, m), 3.60 (2H, t, J=6Hz) |
| 7 | " | 5 | $(CH_2)_3COOCH_3$ | 138~141.5 | 401 $(M+1)^+$ | 0.89 (3H, br. t, J=6Hz), 1.00~2.16 (20H, m), 2.36~2.60 (4H, m), 2.88~3.20 (4H, m), 3.63 (3H, t, J=7Hz), 3.68 (3H, s) |
| 8 | " | 5 | $COCH_2COOC_2H_5$ | | 414 $(M+1)^+$ | 0.88 (3H, br. t, J=6Hz), 1.00~2.64 (29H, m), 3.12~3.48 (2H, m), 3.30 (2H, s), 3.48~3.80 (2H, m), 4.20 (2H, q, J=7Hz), 7.28 (1H, br. s), 8.20 (1H, br. s) |
| 9 | " | 5 | $COCH_2COOCH_3$ | 75~78 | 400 $(M^+)$ | 0.85 (3H, br. t, J=6Hz), 1.00~2.72 (26H, m), 3.08~3.48 (4H, m), 3.48~4.00 (2H, m), 3.71 (3H, s) |
| 10 | $CO(CH_2)_{10}CH_3$ | 3 | $COCH_2CH_2COOH$ | | 355 $(M+1)^+$ | 0.89 (3H, br. t, J=6Hz), 1.00~2.00 (18H, m), 2.32~2.72 (6H, m), 3.18 (2H, t, J=7Hz), 3.64 (2H, t, J=7Hz) |
| 11 | " | 3 | $COCH_2CH_2COOCH_3$ | 95.5~98.5 | 386 $(M^+)$ | 0.87 (3H, br. t, J=6Hz), 1.08~2.12 (18H, m), 2.28~2.80 (6H, m), 3.12~3.44 (2H, m), 3.56~3.80 (2H, m), 3.66 (3H, s), 6.44 (1H, br. s), 8.52 (1H, br. s) |
| 12 | " | 5 | $COCH_2CH_2COOH$ | 132~136 | 400.2969 | 0.89 (3H, t), 1.1~1.8 (2H, m), 2.57 (2H, t), 3.59 (2H, t) |
| 13 | " | 5 | $COCH_2CH_2COOCH_3$ | 100~101.5 | 414.3123 | 0.90 (3H, t), 1.2~1.4 (18H, m), 1.4~1.8 (6H, m), 2.45 (2H, t), 2.46 (2H, t), 2.60 (2H, t), 3.16 (2H, t), 3.60 (2H, t), 3.66 (3H, s) |
| 14 | H | 5 | " | | 232.1411 | 1.2~2.0 (6H, m), 2.47 (2H, t), 2.60 (2H, t), 3.17 (4H, m), 3.66 (3H, |

TABLE 1-continued $$R^1-N-(CH_2)_m-NH-R^2$$
$$\phantom{R^1-N-}|$$
$$\phantom{R^1-N}OH$$

| No. | R¹ | m | R² | Melting point (°C.) | A | ¹H-NMR δ: ppm |
|---|---|---|---|---|---|---|
| 15 | CO(CH₂)₁₆CH₃ | 5 | COCH₂CH₂COOCH₃ | 111.5~113.5 | 498.4060 | s) 0.90 (3H, t), 1.2~1.4 (30H, m), 1.4~1.8 (6H, m), 2.45 (2H, t), 2.47 (2H, t), 2.60 (2H, t), 3.16 (2H, t), 3.60 (2H, t), 3.66 (3H, s) |
| 16 | CO(CH₂)₁₅CH₃ | 5 | " | 109.5~110.5 | 484.3908 | 0.90 (3H, t), 1.2~1.4 (28H, m), 1.4~1.8 (6H, m), 2.45 (2H, t), 2.47 (2H, t), 2.60 (2H, t), 3.16 (2H, t), 3.60 (2H, t), 3.66 (3H, s) |
| 17 | CO(CH₂)₁₄CH₃ | 5 | " | 111.0~111.5 | 470.3702 | 0.90 (3H, t), 1.2~1.4 (26H, m), 1.4~1.8 (6H, m), 2.45 (2H, t), 2.46 (2H, t), 2.60 (2H, t), 3.16 (2H, t), 3.60 (2H, t), 3.66 (3H, s) |
| 18 | CO(CH₂)₁₂i-Pr | 5 | " | 98.0~98.5 | 470.3693 | 0.87 (6H, d), 1.1~1.4 (22H, m), 1.4~1.8 (7H, m), 2.46 (2H, t), 2.47 (2H, t), 2.59 (2H, t), 3.15 (2H, t), 3.59 (2H, t), 3.65 (3H, s) |
| 19 | CO(CH₂)₁₃CH₃ | 5 | COCH₂CH₂COOCH₃ | 103.5~104.5 | 456.3581 | 0.89 (3H, t), 1.2~1.4 (24H, m), 1.4~1.8 (6H, m), 2.44 (2H, t), 2.46 (2H, t), 2.59 (2H, t), 3.15 (2H, t), 3.59 (2H, t), 3.65 (3H, s) |
| 20 | CO(CH₂)₁₁i-Pr | 5 | " | 99.0~100.0 | 456.3561 | 0.87 (6H, d), 1.1~1.4 (20H, m), 1.4~1.8 (7H, m), 2.44 (2H, t), 2.46 (2H, t), 2.60 (2H, t), 3.15 (2H, t), 3.59 (2H, t), 3.65 (3H, s) |
| 21 | CO(CH₂)₁₀CHC₂H₅<br>\|<br>CH₃ | 5 | " |  | 456.3549 | 0.86 (3H, t), 0.87 (3H, t), 1.1~1.4 (19H, m), 1.4~1.8 (6H, m), 2.45 (2H, t), 2.47 (2H, t), 2.60 (2H, t), 3.16 (2H, t), 3.60 (2H, t), 3.66 (3H, s) |
| 22 | CO(CH₂)₁₂CH₃ | 5 | " | 106.0~107.0 | 442.3409 | 0.90 (3H, t), 1.2~1.4 (22H, m), 1.4~1.8 (6H, m), 2.45 (2H, t), 2.47 (2H, t), 2.60 (2H, t), 3.16 (2H, t), 3.59 (2H, t), 3.66 (3H, s) |
| 23 | CO(CH₂)₁₀i-Pr | 5 | COCH₂CH₂COOCH₃ | 88.0~89.0 | 442.3376 | 0.88 (6H, d), 1.1~1.4 (18H, m), 1.4~1.8 (7H, m), 2.45 (2H, t), 2.46 (2H, t), 2.60 (2H, t), 3.16 (2H, t), 3.60 (2H, t), 3.66 (3H, s) |
| 24 | CO(CH₂)₁₁CH₃ | 5 | " | 100.5~101.5 | 428.3220 | 0.90 (3H, t), 1.2~4.4 (20H, m), 1.4~1.8 (6H, m), 2.45 (2H, t), 2.47 (2H, t), 2.60 (2H, t), 3.16 (2H, t), 3.60 (2H, t), 3.66 (3H, s) |
| 25 | CO(CH₂)₉i-Pr | 5 | " |  | 428.3284 | 0.88 (6H, d), 1.1~1.4 (16H, m), 1.4~1.8 (7H, m), 2.45 (2H, t), 2.47 (2H, t), 2.60 (2H, t), 3.16 (2H, t), 3.60 (2H, t), 3.65 (3H, s) |

TABLE 1-continued $$R^1-N-(CH_2)_m-NH-R^2$$
$$\phantom{R^1-N-}|$$
$$\phantom{R^1-N}OH$$

| No. | $R^1$ | m | $R^2$ | Melting point (°C.) | A | $^1$H-NMR δ: ppm |
|---|---|---|---|---|---|---|
| 26 | CO(CH$_2$)$_8$CHC$_2$H$_5$<br>\|<br>CH$_3$ | 5 | " | | 428.3259 | 0.86 (3H, t), 0.87 (3H, t), 1.1~1.4 (17H, m), 1.4~1.8 (6H, m), 2.44 (2H, t), 2.46 (2H, t), 2.59 (2H, t), 3.15 (2H, t), 3.59 (2H, t), 3.65 (3H, s) |
| 27 | CO(CH$_2$)$_8$i-Pr | 5 | COCH$_2$CH$_2$COOCH$_3$ | | 414.3072 | 0.88 (6H, d), 1.1~1.4 (14H, m), 1.4~1.8 (7H, m), 2.45 (2H, t), 2.47 (2H, t), 2.60 (2H, t), 3.16 (2H, t), 3.60 (2H, t), 3.66 (3H, s) |
| 28 | CO(CH$_2$)$_8$CH$_3$ | 5 | " | 95.5~96.5 | 386.2792 | 0.89 (3H, t), 1.2~1.4 (14H, m), 1.4~1.7 (6H, m), 2.44 (2H, t), 2.46 (2H, t), 2.59 (2H, t), 3.15 (2H, t), 3.59 (2H, t), 3.65 (3H, s) |
| 29 | CO(CH$_2$)$_6$CH$_3$ | 5 | " | 89.5~90.5 | 358.2469 | 0.90 (3H, t), 1.2~1.4 (10H, m), 1.4~1.7 (6H, m), 2.45 (2H, t), 2.47 (2H, t), 2.60 (2H, t), 3.16 (2H, t), 3.60 (2H, t), 3.66 (3H, s) |
| 30 | CO(CH$_2$)$_4$CH$_3$ | 5 | " | 88.0~89.0 | 330.2138 | 0.92 (3H, t), 1.2~1.4 (6H, m), 1.4~1.7 (6H, m), 2.45 (2H, t), 2.47 (2H, t), 2.60 (2H, t), 3.16 (2H, t), 3.60 (2H, t), 3.66 (3H, s) |
| 31 | CO(CH$_2$)$_2$CH$_3$ | 5 | COCH$_2$CH$_2$COOCH$_3$ | | 302.1869 | 0.96 (3H, t), 1.2~1.4 (2H, m), 1.4~1.8 (6H, m), 2.44 (2H, t), 2.47 (2H, t), 2.60 (2H, t), 3.16 (2H, t), 3.59 (2H, t), 3.60 (2H, t), 3.66 (3H, s) |
| 32 | COCH$_2$CH$_3$ | 5 | " | | 288.1692 | 1.09 (3H, t), 1.2~1.4 (2H, m), 1.4~1.8 (4H, m), 2.46 (2H, t) 2.47 (2H, q), 2.59 (2H, t), 3.15 (2H, t), 3.65 (3H, s) |
| 33 | COCH$_3$ | 5 | " | | 274.1512 | 1.2~1.4 (2H, m), 1.4~1.8 (4H, m), 2.09 (3H, s), 2.47 (2H, t), 2.60 (2H, t), 3.16 (2H, t), 3.59 (2H, t), 3.66 (3H, s) |

The compound numbers correspond to the example numbers.
The data in column A are as follows:
EIMS (m/z): for compound Nos. 4, 5, 8, 9, and 11.
SIMS (m/z): for compound Nos. 1, 2, 3, 6, 7 and 10.
HR-MS (M$^+$): for compound Nos. 12 to 33.
The solvent for $^1$H-NMR are as follows:
CDCl$_3$ + CD$_3$OD: for compound Nos. 1, 3 and 6.
CDCl$_3$: for compound Nos. 2, 4, 5, 8, 9 and 11
CD$_3$OD: for compound Nos. 7, 10, 12 to 33.

Compounds (I) strongly inhibit lipoxygenases. Therefore, Compounds (I) are useful in the treatment and/or prevention of diseases caused by lipoxygenase-mediated metabolites, for example, various allergic diseases (allergic rhinitis, urticaria, etc.), ischemic heart diseases, hypertension, ischemic encephalopathy, arteriosclerosis and inflammation. For such purposes, they can be administered to patients either orally or nonorally (by injection, cutaneous application, inhalation, etc.), while the dose should be decided depending on the therapeutic effect desired, route of administration, treatment period, age, body weight and other factors. For the administration, Compounds (I) are generally used in the form of the pharmaceutical composition such as tablets, pills, powders, granules, capsules, suppositories, injections and so on, although they may also be used as such. Typical examples of the pharmaceutically acceptable carriers to be used in such pharmaceutical compositions include lactose, dextrose, sucrose, sorbitol, mannitol, glucose, cellulose, cyclodextrin, talc, starch, methylcellulose, gelatin, gum arabic, polyethylene glycol, carboxymethylcellulose, hydroxypropylcellulose, sodium benzoate, sodium hydrogen sulfite, aluminum stearate, magnesium stearate, mineral oil, vegetable oil, white vaseline or liquid paraffin. They may suitably be selected depending on the kind of preparation.

Hereinafter, the present invention will be described in greater detail with reference to examples which should by no means be construed as limiting the present invention.

The following test examples demonstrate the lipoxygenase inhibiting activity of the compounds of the present invention. Unless otherwise specified, all mixing ratios of mixed solvents are by volume.

TEST EXAMPLE 1

The compounds listed in Table 2 were tested in vitro for their lipoxygenase inhibiting activity in the following manner: a) Leukocyte 5-lipoxygenase inhibiting activity The method of B.A. Jakschik et al. *Biochem. Biophys. Res. Commun.*, 95, 103 (1980) was modified. Thus, rat basophilic leukemia cells (RBL-1, ATCC No. CRL 1378) were used as the 5-lipoxygenase source. These cells were brought into contact with the test compound in 60 μl of 0.17 M Tris-hydrochloride buffer (pH 7.4) containing 1.7 M calcium chloride, 3.3 mM adenosine triphosphate and 1 mM glutathione at 37° C. for 5 minutes, then 50 μl of 60 μM arachidonic acid was added and the enzymatic reaction was allowed to proceed at 37° C. for 5 minutes. Thereafter, 200 μl of methanol and 13-hydroxylinolic acid (internal standard) were added. After sufficient shaking, the mixture was allowed to stand at −20° C. for 30 minutes and then centrifuged for 10 minutes (12,000 revolutions per minute) to collect the supernatant. The supernatant was evaporated to dryness under a nitrogen gas stream. To the residue was added 200 μl of 75% aqueous methanol and 100 μl of the resultant solution was subjected to high performance liquid chromatography for the determination of 5-HETE (5-hydroxyeicosatetraenoic acid). 5-HETE was assayed on the basis of the absorption at 234 nm as measured by ultraviolet absorption monitoring. The yield of 5-HETE was calculated from the peak area corrected in comparison with the peak of the internal standard. The test compound concentration was varied and the inhibitory activity of the compound was expressed in terms of the compound concentration required for 50% inhibition of the enzymatic activity. (b) Platelet 12-lipoxygenase inhibiting activity The method of D.H. Nugtern et al. *Biochem. Biophys. Acta*, 380, 299 (1975) was modified. Thus, a bovine platelet-derived preparation was used as the 12-lipoxygenase source. This enzyme preparation and the test compound were brought into contact with each other in 60 μl of 0.17 M Tris-hydrochloride buffer (pH 7.4) at 30° C. for 5 minutes, 50 μl of 60 μM arachidonic acid was then added and the enzymatic reaction was allowed to proceed at 30° C. for 10 minutes. Thereafter, 200 μl of methanol and 13-hydroxylinolic acid (internal standard) were added and, after sufficient shaking, the mixture was allowed to stand at −20° C. for 30 minutes. The supernatant was collected by centrifugation (12,000 revolutions per minute, 10 minutes). This supernatant was evaporated to dryness under a nitrogen gas stream. To the residue was added 200 μl of 75% aqueous methanol and 100 μl of the resultant solution was subjected to high performance liquid chromatography for the determination of 12-HETE (12-hydroxyeicosapetraenoic acid). 12-HETE was assayed by ultraviolet absorption monitoring at 234 nm. The yield of 12-HETE was calculated from the peak area corrected in comparison with the peak of the internal standard. The test compound concentration was varied and the inhibitory activity of the compound was expressed in terms of the compound concentration required for 50% inhibition of the enzymatic activity.

The results thus obtained are shown in Table 2.

TABLE 2

| Compound No. | Inhibitory Activity IC$_{50}$ (μM) | |
|---|---|---|
| | 5-Lipoxygenase | 12-Lipoxygenase |
| 2 | 0.01 | 3.3 |
| 6 | 0.56 | |
| 7 | 0.052 | |
| 8 | 0.025 | 0.012 |
| 9 | 0.054 | 0.011 |
| 10 | 0.27 | 7.0 |
| 11 | 0.012 | |

TEST EXAMPLE 2

The compounds listed in Table 3 were tested for their lipoxygenase inhibiting activity by the following methods:

(a') 5-Lipoxygenase inhibiting activity

Essentially, the same method described in the above (a) was used. Thus, rat basophilic leukemia cells (RBL-1, ATCC No. CRL 1378) were used as the 5-lipoxygenase source. These cells were contacted with the test compound in 30 μl of 0.17 M Tris-hydrochloride buffer (pH 7.4) containing 1.7 M calcium chloride, 3.3 mM adenosine triphosphate and 1 mM glutathione at 37° C. for 5 minutes. Then, 25 μl of 27 μM [$^{14}$C]-arachidonic acid was added and the enzymatic reaction was allowed to proceed at 37° C. for 5 minutes. To the reaction mixture was added 50 μl of ethyl acetate/methanol/0.2 M citric acid (30/4/1), and the whole mixture was stirred. The reaction product extracted into the ethyl acetate layer was separated by silica gel thin layer chromatography [Merck Art 5631: developing solvent; petroleum ether/ethyl ether/acetic acid (50/50/1)]. The site of the product [$^{14}$C]-5-hydroxy-6,8,11,14-eicosatetraenoic acid was detected by autoradiography, the gel portion corresponding to the site was scraped off and assayed for $^{14}$C using a liquid scintillation counter, and the yield of the product was determined. The test compound concentration was varied and the inhibitory activity of the test compound was expressed in terms of the concentration required for 50% inhibition of the enzymatic activity.

(b') Platelet 12-lipoxygenase inhibiting activity

Essentially the same procedure described in the above (b) was used. Thus, a bovine platelet-derived preparation was used as the 12-lipoxygenase source. This lipoxygenase preparation was contacted with the test compound in 30 μl of 0.17 M Tris-hydrochloride buffer (pH 7.4) at 30° C. for 5 minutes, 25 μl of 20 μM [$^{14}$C]-arachidonic acid was then added, and the enzymatic reaction was allowed to proceed at 30° C. for 10 minutes. Then, 50 μl of ethyl acetate/methanol/0.2 M citric acid (30/4/1) was added to the reaction mixture, and the whole mixture was stirred. The reaction product extracted into the ethyl acetate layer was separated by silica gel thin layer chromatography [Merck Art 5631: developing solvent; ligroin/ethyl ether/acetic acid (50/50/1)]. The site of the product [$^{14}$C]-12-hydroxy-5,8,10,14-eicosatetraenoic acid was detected by autoradiography, the gel portion corresponding to the site was scraped off and assayed for $^{14}$C with a liquid scintillation counter, and the product yield was determined. The test compound concentration was varied and the inhibitory activity of the compound was expressed in terms of the concentration required for 50% inhibition of the enzymatic activity.

The thus-obtained results, which are shown in Table 3, clearly indicate that the compounds according to the present invention exert inhibitory activity on both the enzymes 5-lipoxygenase and 12-lipoxygenase. From the comparison with the known lipoxygenase inhibitors BW-755C [3-amino-1-(3-trifluoromethylphenyl)-2-pyrazoline hydrochloride] and AA-861 [2-(12-hydroxy-dodeca-5,10-diynyl)-3,5,6-trimethyl-1,4-benzoquinone], it can be seen that the compounds according to the present invention are superior in 5-lipoxygenase and 12-lipoxygenase inhibiting activity as compared with BW-755C and AA-861.

TABLE 3

| Compound No. | Inhibitory Activity $IC_{50}$ (μM) | |
| --- | --- | --- |
| | 5-Lipoxygenase | 12-Lipoxygenase |
| 12 | 1.87 | 0.035 |
| 13 | 0.055 | 0.014 |
| 15 | 0.80 | 32 |
| 17 | 0.47 | 1.0 |
| 21 | 0.36 | 0.31 |
| 23 | 0.30 | 0.056 |
| 24 | 0.19 | 0.036 |
| 27 | 0.089 | 0.033 |
| BW-755C | 6.5 | 8.8 |
| AA-861 | 0.68 | 450 |

The following examples are further illustrative of the present invention. Unless otherwise specified, all mixing ratios of mixed solvents are by volume.

EXAMPLE 1

A solution prepared by dissolving 170 mg of metallic sodium in 5.2 ml of ethanol was added to a solution of 2.57 g (7.39 mmol) of Compound (IV)a [m=5, $R^2$=CO(CH$_2$)$_{10}$CH$_3$] prepared by the procedure of Reference Example 4 and 0.82 g (7.39 mmol) of (Z)-2-furaldehyde oxime in ethanol, and the mixture was stirred at 40° C. for 3.5 hours. The solvent was then distilled off under reduced pressure, chloroform was added to the residue, and the resultant solution was washed with water and dried over anhydrous magnesium sulfate. The solvent was distilled off under reduced pressure, and the residue was purified by silica gel column chromatography (1% methanol/chloroform) to give 1.39 g (yields: 50%) of Compound (V)a [m=5, $R^2$=CO(CH$_2$)$_{10}$CH$_3$].

The above obtained Compound (V)a had the following physicochemical properties: $^1$H-NMR (in CDCl$_3$), δ (ppm): 0.76–1.00 (3H, m), 1.04–2.24 (26H, m), 3.12–3.36 (2H, m), 3.90 (2H, t, J=7Hz), 5.56 (1H, br s), 6.56 (1H, m), 7.40–7.80 (3H, m).

970 mg (2.57 mmol) of the above Compound (V)a was suspended in a mixed solvent composed of 30 ml of methanol and 30 ml of water, 178 mg (2.57 mmol) of hydroxylamine hydrochloride was added, and the mixture was stirred at 60° C. for 2.5 hours. The reaction mixture was adjusted to pH 8–9 by addition of 3 ml of 1 N aqueous sodium hydroxide and then extracted with chloroform. The chloroform layer was washed with water and then dried over anhydrous magnesium sulfate. The solvent was distilled off under reduced pressure, and the residue was purified by silica gel column chromatography (eluent: chloroform containing 3% methanol) to give 650 mg (yield: 84%) of Compound No. 1.

Typical physicochemical properties of Compound No. 1 are shown in Table 1.

EXAMPLE 2

550 mg (1.83 mmol) of Compound No. 1 obtained in Example 1 was dissolved in 30 ml of THF, then 0.56 ml (4.6 mmol) of carbomethoxypropionyl chloride was added, and the mixture was stirred at room temperature for 2.5 hours. The reaction mixture was washed with water and dried over anhydrous magnesium sulfate. Thereafter, the solvent was distilled off under reduced pressure, and the residue was purified by silica gel column chromatography (eluent: chloroform containing 2% methanol) to give 405 mg (yield: 54%) of Compound No. 2.

Typical physicochemical properties of Compound No. 2 are shown in Table 1.

EXAMPLE 3

300 mg (0.72 mmol) of Compound No. 2 obtained in Example 2 was dissolved in 10 ml of methanol, then 3.6 ml of 1 N sodium hydroxide was added, and the mixture was stirred at room temperature for 2.5 hours. The reaction mixture was adjusted to pH 1 to 2 with 1 N hydrochloric acid, and the resultant precipitate was collected by filtration. Thus was obtained 223 mg (yield: 77%) of Compound No. 3.

Typical physicochemical properties of Compound No. 3 are shown in Table 1.

EXAMPLE 4

40 mg (0.1 mmol) of Compound No. 3 obtained in Example 3 was dissolved in 4 ml of isopropyl alcohol, then hydrogen chloride gas was passed through the solution with ice cooling until a state of saturation was reached, and the resultant mixture was stirred at room temperature for 2 hours. The reaction mixture was washed with water and dried over anhydrous magnesium sulfate, and the solvent was distilled off under reduced pressure to give 44 mg (yield: 100%) of Compound No. 4.

Typical physicochemical properties of Compound No. 4 are shown in Table 1.

EXAMPLE 5

60 mg (0.2 mmol) of Compound No. 1 obtained in Example 1 was dissolved in 1 ml of THF, then 0.04 ml (0.4 mmol) of acetic anhydride and 0.03 ml (0.4 mmol) of pyridine were added, and the mixture was stirred at room temperature for 2 hours. The reaction mixture was washed in sequence with saturated aqueous sodium hydrogen carbonate, 5% aqueous citric acid and saturated sodium chloride and then dried over anhydrous magnesium sulfate, and the solvent was distilled off under reduced pressure. The residue was recrystallized from ethyl acetate-n-hexane to give 35 mg (yield: 51%) of Compound No. 5.

Typical physicochemical properties of Compound No. 5 are shown in Table 1.

EXAMPLE 6

150 mg (0.5 mmol) of Compound (a) obtained in Reference Example 1 and 0.85 ml of succinic semialdehyde were dissolved in 5 ml of ethanol, then 0.5 ml of 1 N hydrochloric acid was added, 167 mg of sodium cyanoborohydride was further added with ice cooling, and the mixture was stirred overnight. The reaction mixture was adjusted to pH 1 to 2 with 1 N hydrochloric acid, the solvent was then distilled off under reduced pressure, and the residue was purified by silica gel column chromatography (eluent: chloroform/methanol/28% aqueous ammonia=90/10/1) and then recrystallized by addition of a mixed solvent composed of ethyl acetate and ethanol to give 81 mg (yield: 42%) of Compound No. 6.

Typical physicochemical properties of Compound No. 6 are shown in Table 1.

EXAMPLE 7

The same procedure as in Example 4 was repeated except for using Compound No. 6 obtained in Example 6 in place of Compound No. 3, to give 22 mg (yield: 82.5%) of the hydrochloride salt of Compound No. 7.

Typical physicochemical properties of the hydrochloride salt of Compound No. 7 are shown in Table 1.

EXAMPLE 8

The same procedure as in Example 1 was followed using, in place of Compound (IV)a, the compound obtained in the same manner as in Reference Example 4 except that Compound (IX)a ($R^{3a}$=$C_2H_5$, l=1, m=5) was used in place of Compound (III)a. Thus was obtained the hydroxylamine (XI)a ($R^{3a}$=$CH_3CH_2$, l=1, m=5) with a yield of 0.36 g. The same procedure as in Example 2 was repeated except for using Compound (XII)a in place of Compound No. 1, and 350 mg of n-dodecanoyl chloride in place of carbomethoxypropionyl chloride, to give 93 mg (yield: 14%) of Compound No. 8.

Typical physicochemical properties of Compound No. 8 are shown in Table 1.

EXAMPLE 9

The same procedure as in Example 4 was followed using, in place of Compound No. 3, the compound obtained in the same manner as in Example 3 except that 70 mg of Compound No. 8 obtained in Example 8 was used in place of Compound No. 2. Thus was obtained 27 mg (yield: 42%) of Compound No. 9.

Typical physicochemical properties of Compound No. 9 are shown in Table 1.

EXAMPLE 10

The same procedure as in Example 5 was repeated except for using 172 mg of N-(3-hydroxyaminopropyl)-succinimide hydrochloride (Compound (b)) obtained in Reference Example 2 in place of Compound No. 1, and using 1.14 g of lauric anhydride in place of acetic anhydride. The procedure of Example 3 was then followed using the thus-obtained compound in place of Compound No. 2 to give 210 mg (yield: 59.3%) of Compound No. 10.

Typical physicochemical properties of Compound No. 10 are shown in Table 1.

EXAMPLE 11

The same procedure as in Example 4 was repeated except for using 100 mg of Compound No. 10 obtained in Example 10 in place of Compound No. 3, to give 70 mg (yield: 67.4%) of Compound No. 11.

Typical physicochemical properties of Compound No. 11 are shown in Table 1.

EXAMPLE 12

To 9 g of sodium hydride washed with hexane dehydrated by distillation, 60 ml of tetrahydrofuran dehydrated by distillation was added, then 15 g of succinimide was added portionwise, and the resultant mixture was stirred at room temperature for 1 hour. Separately, 60 g of dibromopentane was dissolved in 60 ml of tetrahydrofuran dehydrated by distillation and the solution was refluxed under heating. To this refluxing solution was added the above-prepared sodium salt of succinimide portionwise over 2 hours. After 24 hours of refluxing, the reaction mixture was filtered, and the filtrate was concentrated under reduced pressure. The concentrate was applied to a column of 300 g of silica gel (Wakogel C-200, product of Wako Pure Chemical Ind.) suspended in advance in n-hexane-chloroform (3:1). Elution was carried out with one liter each of 3:1, 2:1, 2:3, 1:3 and 1:4 n-hexane-chloroform mixtures (eluents). Each eluate fraction was subjected to silica gel thin layer chromatography for checking the elution of the desired product. The product-containing fractions were combined and concentrated to give 20.6 g (yield: 55%) of ω-bromoalkylsuccinimide.

HR-MS: Found: 249.0182, Calculated for $C_9H_{14}NO_2Br$: 249.0189.

$^1$H-NMR ($CDCl_3$): 1.2–2.2 (8H, m), 2.72 (4H, s), 3.41 (2H, t), 3.54 (2H, t).

10 g of the ω-bromoalkylsuccinimide obtained was dissolved in 25 ml of nitropropane, and the solution was stirred in a nitrogen atmosphere with heating at 65° C. Silver nitrite (7.3 g) was added portionwise over 1 hour, the temperature was then raised to 125° C., the reaction mixture was stirred for an additional 5 hours and then filtered, and the filtrate was concentrated. The concentrate was applied to a column of 300 g of silica gel (Wakogel C-200, product of Wako Pure Chemical Ind.) suspended in advance in n-hexane-chloroform (2:1). Elution was performed with one liter of n-hexane-chloroform (2:1), 500 ml each of 1:1, 1:2 and 1:3 n-hexane-chloroform mixtures, 500 ml of chloroform and 500 ml each of 200:1 and 150:1 chloroform-methanol mixtures, in that order. Each eluate fraction was checked for the elution of the desired product by silica gel thin layer chromatography. The product-containing fractions were combined and concentrated to give 4.6 g of ω-nitroalkylsuccinimide (yield: 51%).

HR-MS: Found: 214.0934, Calculated for $C_9H_{14}N_2O_4$: 214.0953, $^1$H-NMR ($CDCl_3$): 1.2–2.4 (6H, m), 2.69 (4H, s), 3.48 (2H, t), 4.37 (2H, t).

The ω-nitroalkylsuccinimide obtained was dissolved in 25 ml of ethanol and, with ice cooling, 18 ml of 10% ammonium chloride was added. Then, 1.2 g of zinc powder was added, the mixture was stirred for 10 minutes and then filtered, and the filtrate was concentrated to dryness. Hot ethanol (20 ml) was added to the residue, and the mixture was filtered. The filtrate was concentrated to dryness to give 1.7 g of a solid containing Compound (XVIII).

To the crude product were added 10 ml of pyridine, 5 g of lauric anhydride and 5 ml of methylene chloride, and the mixture was stirred overnight at room temperature. Water (5 ml) was added to the reaction mixture, and the whole mixture was allowed to stand at room temperature for 1 hour and then extracted with ethyl acetate. The ethyl acetate layer was washed with 2 N hydrochloric acid, saturated aqueous sodium hydrogen carbonate and saturated aqueous sodium chloride in that order and dried over magnesium sulfate. The magnesium sulfate was filtered off, and the filtrate was concentrated to give 5.1 g of a solid. This was applied to a column of 200 g of silica gel (Wakogel C-200, product of Wako Pure Chemical Ind.) suspended in advance in chloroform. Elution was carried out with 300 ml each of 200:1, 160:1, 120:1, 90:1 and 70:1 chloroform-methanol mixtures. Each eluate fraction was checked for the elution of the desired product by silica gel thin layer chromatography. The product-containing fractions were combined and concentrated to give 1.5 g of Compound (XIX)a $R^3=CH_3(CH_2)_{10}$ (yield: 58% from ω-nitrosuccinimide).

HR-MS: Found: 564.4463, Calculated for $C_{33}H_{60}N_2O_5$:564.4502.

$^1$H-NMR (CDCl$_3$): 0.88 (6H, t), 1.1–1.8 (42H, m), 2.1–2.6 (4H, m), 2.73 (4H, s), 3.4–3.8 (4H, m).

To 1.2 g of Compound (XIX)a was added 2 ml of methanol, 2 ml of THF and 4 ml of 1 N sodium hydroxide, and the mixture was allowed to stand at room temperature for 1 hour. The reaction mixture was acidified by addition of 2 N hydrochloric acid, and the resultant precipitate was collected by filtration. Recrystallization of the precipitate (1.0 g) from ethyl acetate gave 288 mg of Compound No. 12 (yield: 34%).

Typical physicochemical properties of Compound No. 12 are shown in Table 1.

EXAMPLE 13

Compound No. 12 (200 mg) was dissolved in 5 ml of methanol, and methyl esterification was carried out by adding a solution of diazomethane in ether. Addition of diazomethane was continued until the nitrogen gas evolution ceased and the reaction mixture retained the yellow color of diazomethane slightly. The reaction mixture was concentrated, and the residual solid (207 mg) was recrystallized from ethyl acetate to give 192 mg of Compound No. 13 (yield: 93%).

Typical physicochemical properties of Compound No. 13 are shown in Table 1.

EXAMPLE 14

The same procedure as in Example 13 was repeated except for using, in place of Compound No. 12 of Example 13, a compound obtained in the same manner as in Example 12 except that a solid containing Compound (XVIII) obtained in Example 12 was used in place of Compound (XIX)a in Example 12, to give Compound No. 14.

Typical physicochemical properties of Compound No. 14 are shown in Table 1.

EXAMPLES 15 TO 33

Compounds Nos. 15 to 33 shown in Table 1 were synthesized in the same procedures as in Examples 12 and 13 except for using the respective acid anhydrides listed in Table 4.

TABLE 4

| Example | Acid anhydride |
|---|---|
| 15 | $[CH_3(CH_2)_{16}CO]_2O$ |
| 16 | $[CH_3(CH_2)_{15}CO]_2O$ |
| 17 | $[CH_3(CH_2)_{14}CO]_2O$ |
| 18 | $[CH_3CH(CH_2)_{12}CO]_2O$ with $CH_3$ branch |
| 19 | $[CH_3(CH_2)_{13}CO]_2O$ |
| 20 | $[CH_3CH(CH_2)_{11}CO]_2O$ with $CH_3$ branch |

TABLE 4-continued

| Example | Acid anhydride |
|---|---|
| 21 | $[CH_3CH_2CH(CH_2)_{11}CO]_2O$ with $CH_3$ branch |
| 22 | $[CH_3(CH_2)_{12}CO]_2O$ |
| 23 | $[CH_3CH(CH_2)_{10}CO]_2O$ with $CH_3$ branch |
| 24 | $[CH_3(CH_2)_{11}CO]_2O$ |
| 25 | $[CH_3CH(CH_2)_9CO]_2O$ with $CH_3$ branch |
| 26 | $[CH_3CH_2CH(CH_2)_8CO]_2O$ with $CH_3$ branch |
| 27 | $[CH_3CH(CH_2)_8CO]_2O$ with $CH_3$ branch |
| 28 | $[CH_3(CH_2)_8CO]_2O$ |
| 29 | $[CH_3(CH_2)_6CO]_2O$ |
| 30 | $[CH_3(CH_2)_4CO]_2O$ |
| 31 | $[CH_3(CH_2)_2CO]_2O$ |
| 32 | $(CH_3CH_2CO)_2O$ |
| 33 | $(CH_3CO)_2O$ |

EXAMPLE 34

Production of Compounds (I) by fermentative method

Micromonospora sp. K-216 (FERM BP-1406) was used as a seed strain. The seed culture medium used contained 10 g/liter of glucose, 10 g/liter of soluble starch, 3 g/liter of beef extract, 5 g/liter of yeast extract, 5 g/liter of Bacto-tryptone and 2 g/liter of calcium carbonate and was adjusted to pH 7.2 (before sterilization). The fermentation medium used contained 10 g/liter of glucose, 20 g/liter of lactose, 15 g/liter of Pharmamedia, 10 g/liter of beef extract, 5 g/liter of yeast extract and 2 g/liter of calcium carbonate and was adjusted to pH 7.2 (before sterilization).

One loopful of the strain was inoculated into 10 ml of the above-mentioned seed culture medium placed in a 50-ml culture tube, and shake culture was carried out at 28° C. for 4 days.

A 5-ml portion of the culture fluid was transferred to a 300-ml erlenmeyer flask containing 50 ml of the seed culture medium, and culture was performed at 28° C. for 2 days. A 50-ml portion of the culture fluid thus obtained was inoculated into 500 ml of the seed culture medium placed in a 2-liter erlenmeyer flask, and culture was carried out at 28° C. for 1 day. A total of 1.5 liters of the seed culture fluid prepared in that manner was inoculated into 15 liters of the seed culture medium in a 30-liter stainless steel jar fermenter. Cultivation was conducted under the following conditions: 28° C., 300 revolutions per minute, aeration 15 liters per minute. The culture fluid was sampled at timed intervals and the difference in optical density at 660 nm ($\Delta OD_{660}$) between a 40-fold dilution (diluent: water) of each culture fluid sample and a 40-fold dilution of the medium as such without inoculation was determined. When the difference $\Delta OD_{660}$ had reached 0.07, 7.5 liters of the seed culture fluid was transferred to a 200-liter stainless steel jar fermenter containing 150 liters of the above-mentioned fermentation medium. Cultivation was performed at 25° C. for four days, 180 revolutions per minute and an aeration rate of 150 liters per minute while pH was adjusted so that it would not exceed 7.8.

The culture fluid (150 liters) obtained in the above manner was centrifuged (15,000 rpm), and the supernatant was adjusted to pH 3.5 with concentrated hydrochloric acid and allowed to stand overnight at room temperature. The resultant precipitate was collected by continuous centrifugation (15,000 rpm) and dissolved in 10 liters of a methanolic solution containing 167 ml of concentrated hydrochloric acid, and the solution was stirred at 50° C. for 3 hours. The insoluble matter was filtered off, and the filtrate was concentrated to 250 ml under reduced pressure and applied to a column packed with 2 liters of Diaion HP-10 (product of Mitsubishi Kasei). Elution was carried out with 10 liters of water and then with 15 liters of methanol. The methanol eluate was concentrated to dryness and the solid was dissolved in 100 ml of chloroform-methanol (9:1). The solution was applied to a column packed with 500 g of silica gel (average particle size: 60 to 230 μm) and elution was carried out with 3 liters of chloroform, 3 liters of chloroform-methanol (9:1) and 3 liters of chloroform-methanol (1:1) in that order. The chloroform-methanol (9:1) eluate fractions were combined and concentrated to dryness. The solid obtained was dissolved in 50 ml of chloroform and applied to a column packed with 250 g of silica gel (average particle size: 40 to 63 μm). Elution was performed with 2 liters each of chloroform and 99:1, 99:8 and 95:5 chloroform-methanol mixtures in that order. Each eluate fraction was checked by silica gel thin layer chromatography [Merck Art. 5628, developing solvent: chloroform-methanol (9:1)]. Those fractions which gave a spot located at $R_f=0.57$ and capable of developing a color upon exposure to iodine on the silica gel thin layer were combined and concentrated to dryness to give 4.52 g of a brown solid. Ethyl acetate (40 ml) was added to this solid, the mixture was heated for dissolution of the solid, and the solution was allowed to stand at $-20°$ C. The resultant precipitate was collected by filtration and recrystallized from 25 ml of ethyl acetate to give 2.84 g of colorless crystalline substance.

A 400-mg portion of the obtained substance was dissolved in 4 ml of pyridine, then 1 ml of benzoic anhydride was added, and the mixture was stirred for about 12 hours at room temperature. Ethyl acetate (30 ml) was added to the reaction mixture, the ethyl acetate layer was washed with 5% aqueous sodium hydrogen carbonate, 5% aqueous citric acid and saturated aqueous sodium chloride and then dried over anhydrous sodium sulfate. The ethyl acetate was removed under reduced pressure to give 512 mg of a benzoylated products. These products were subjected to reversed-phase liquid chromatography [column: YMC AM312 (ODS) 6×150 mm, eluent: 90% methanol, flow rate: 1 ml/minute, detection: UV (230 nm)] to give 14 peak fractions. Each peak component was refluxed under heating in methanol for debenzoylation to give Compound Nos. 13 and 15 to 27.

REFERENCE EXAMPLE 1

Preparation of
N-(5-aminopentyl)-n-dodecanoylhydroxamic acid
(Compound (a))

The same procedure as in Example 1 was repeated except for using 4.89 g (16.5 mmol) of N-(5-bromopentyl)phthalimide in place of Compound (IV)a to give 1.74 g (yield: 37%) of the corresponding hydroxylamine.

The above hydroxylamine compound had the following physicochemical properties.

$^1$H-NMR (CD$_3$OD), δ (ppm): 1.24–2.00 (6H, m), 3.22 (2H, t J=8Hz), 3.70 (2H, t, J=7Hz), 7.83 (4H, s).

SIMS (m/z): 249 (M+1)$^+$.

The same procedure as in Example 2 was repeated except for using 762 mg (3 mmol) of the hydrochloride of the above hydroxylamine compound in place of Compound No. 1, and using 656 mg of n-dodecanoyl chloride in place of carbomethoxypropionyl chloride, to give 1.07 g (yield: 83%) of n-dodecanoylhydroxamic acid.

$^1$H-NMR (CDCl$_3$) δ (ppm): 0.90 (3H, br. t, J=7Hz), 1.04–2.05 (26H, m), 3.50–3.88 (4H, m), 7.64–8.00 (4H, m).

724 mg (1.68 mmol) of the above n-dodecanoylhydroxamic acid was dissolved in 7 ml of dioxane, then 0.17 ml of hydrazine hydrate was added, and the mixture was stirred at room temperature for 2 hours. The reaction mixture was washed with water and dried over anhydrous magnesium sulfate, and the solvent was distilled off under reduced pressure. The residue was purified by silica gel column chromatography (eluent: methanol/chloroform/28% aqueous ammonia=10/90/0.5) and then recrystallized from ethyl acetate to obtain 116 mg (yield: 23%) of Compound (a).

Compound (a) had the following physicochemical properties.

$^1$H-NMR (CDCl$_3$+CD$_3$OD), δ (ppm): 0.89 (3H, br. t, J=6Hz), 1.00–1.88 (24H, m), 2.22 (2H, t, J=7Hz), 2.48(2H, t, J=7Hz), 2.85 (2H, t, J=7Hz), 3.64 (2H, t, J=7Hz).

REFERENCE EXAMPLE 2

Preparation of N-(3-hydroxyaminopropyl)succinimide hydrochloride (Compound (b))

The same procedure as in Example 1 was repeated except for using 3.05 g (13.9 mmol) of N-(3-bromopropyl)succinimide in place of Compound (IV)a to give 200 mg (yield 87%) of Compound (b).

Compound (b) had the following physicochemical properties.

$^1$H-NMR (CDCl$_3$), δ (ppm): 1.84 (2H, m), 2.68 (4H, s), 2.91 (2H, t, J=7Hz), 3.60 (2H, t, J=7Hz), 5.04 (1H, br. s).

SIMS (m/s): 173 (M+1)$^+$.

REFERENCE EXAMPLE 3

3 ml (22 mmol) of triethylamine was added to a solution of 2.06 g (20 mmol) of 5-amino-1-pentanol and 4.6 ml (20 mmol) of lauroyl chloride in 100 ml of THF, and the mixture was stirred with ice cooling for 1 hour. The reaction mixture was washed in sequence with 1 N hydrochloric acid, saturated aqueous sodium hydrogen carbonate and saturated aqueous sodium chloride and then dried over anhydrous magnesium sulfate, and the solvent was distilled off under reduced pressure. The residue was recrystallized from ethyl acetate to give 2.99 g (yield: 52%) of Compound (III)a [m=5, $R^2$=CO(CH$_2$)$_{10}$CH$_3$].

Compound (III)a had the following physicochemical properties.

$^1$H-NMR (CDCl$_3$), δ (ppm): 0.87 (1H, m), 1.00–2.28 (26H, m), 3.04–3.40 (2H, m), 3.64 (2H, t, J=7Hz), 5.52 (1H, br. s).

SIMS (m/z): 286 (M+1)$^+$.

REFERENCE EXAMPLE 4

2.85 g (10 mmol) of Compound (III)a obtained in Reference Example 3 was dissolved in methylene chloride, then 5.14 g (20 mmol) of triphenylphosphine and 3.56 g (20 mmol) of NBS were added to the solution with ice cooling, and the mixture was stirred for about 12 hours at room temperature. The solvent was distilled off under reduced pressure, and the residue was purified by silica gel column chromatography (eluent: toluene containing 8% acetone) to give 2.60 g (yield: 75%) of Compound (IV)a [m=5, R$^2$=CO(CH$_2$)$_{10}$ CH$_3$].

The obtained Compound (IV)a had the following physicochemical properties.

$^1$H-NMR (CDCl$_3$), δ (ppm): 0.88 (3H, br. t, J=7Hz), 1.00–2.28 (26H, m), 3.08–3.36 (2H, m), 3.40 (2H, t, J=7Hz), 5.5 (1H, br. s).

SIMS (m/z): 348 (M+1)$^+$.

From the above results, it can be seen that Compounds (I) and salts thereof have 5- and 12-lipoxygenase inhibiting activity and can be used in the prevention and/or treatment of diseases caused by lipoxygenase-mediated metabolites.

While the invention has been described in detail and with reference to specific embodiments thereof, it will be apparent to one skilled in the kart that various changes and modifications can be made therein without departing from the spirit and scope thereof.

What is claimed is:

1. A hydroxamic acid compound represented by the formula (I) or a salt thereof:

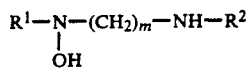

wherein R$^1$ represent a hydrogen atom, or a substituted or unsubstituted alkanoyl group, R$^2$ represents an alkanoyl, substituted lower alkanoyl or substituted lower alkyl group, and m represents an integer of 3 to 7, wherein the substituent on the substituted alkanoyl, the substituted lower alkanoyl and the substituted lower alkyl is a hydroxycarbonyl group or a lower alkoxycarbonyl group.

2. A compound according to claim 1, wherein the alkyl moiety of the alkanoyl group includes a straight or branched alkyl group having 1 to 17 carbon atoms.

3. A compound according to claim 1, wherein the alkyl moiety of the lower alkanoyl group and the lower alkyl group include an alkyl group having 1 to 5 carbon atoms.

4. A compound according to claim 1, wherein the lower alkoxy moiety of the lower alkoxycarbonyl group is an alkoxy group having 1 to 5 carbon atoms.

5. A compound according to claim 1, wherein the salt is selected from the group consisting of acid addition salt, ammonium salt, salt of an alkali metal, salt of an alkaline earth metal, salt of an organic amine and salt of a basic amino acid.

6. A pharmaceutical composition comprising a pharmaceutically acceptable carrier and, as an active ingredient, an effective amount of a hydroxamic acid compound defined in claim 1.

7. A method for treating diseases caused by lipoxygenase-mediated metabolites, which comprises administering to a human an effective amount of a pharmaceutical composition comprising a hydroxamic acid compound defined in claim 1 and a pharmaceutically acceptable carrier.

* * * * *